(12) United States Patent
Shewey et al.

(10) Patent No.: US 8,574,028 B2
(45) Date of Patent: Nov. 5, 2013

(54) GRINDER/POLISHER

(75) Inventors: Charles E. Shewey, Salem, WI (US); Douglas A. Ceckowski, Gurnee, IL (US); Michael F. Hart, Mundelein, IL (US)

(73) Assignee: Illinois Tool Works Inc., Glenview, IL (US)

( * ) Notice: Subject to any disclaimer, the term of this patent is extended or adjusted under 35 U.S.C. 154(b) by 753 days.

(21) Appl. No.: 12/470,757

(22) Filed: May 22, 2009

(65) Prior Publication Data

US 2009/0318059 A1 Dec. 24, 2009

Related U.S. Application Data

(60) Provisional application No. 61/074,455, filed on Jun. 20, 2008.

(51) Int. Cl.
*B24B 49/00* (2012.01)
*B24B 51/00* (2006.01)
*B24B 55/06* (2006.01)

(52) U.S. Cl.
USPC .......... 451/5; 451/9; 451/10; 451/11; 451/14; 451/453

(58) Field of Classification Search
USPC ...................... 451/5, 9–11, 14, 453
See application file for complete search history.

(56) References Cited

U.S. PATENT DOCUMENTS

| | | | |
|---|---|---|---|
| 3,233,370 A * | 2/1966 | Best et al. | 451/286 |
| 4,020,600 A * | 5/1977 | Day | 451/398 |
| 4,459,785 A * | 7/1984 | Zimmer | 451/398 |
| 4,873,792 A | 10/1989 | Linke et al. | |
| 5,800,254 A | 9/1998 | Motley et al. | |
| 5,816,899 A * | 10/1998 | Hart et al. | 451/272 |
| 6,224,474 B1 | 5/2001 | Vander Voort | |
| 7,070,067 B1 | 7/2006 | Buchanan et al. | |

OTHER PUBLICATIONS

Brochure for TegraSystem from Struers Inc., Sep. 2006.
Brochure for Saphir 560 Specimen Preparation System from Mager Scientific, Inc., Jan. 2006.
Brochure for Mecatech 334 from Presi, Apr. 2006.
Brochure for Saphir 550 from ATM GmbH, Dec. 2007.
International Search Report for PCT/US2009/046190 dated Feb. 9, 2010.

* cited by examiner

*Primary Examiner* — Dung Van Nguyen
(74) *Attorney, Agent, or Firm* — Levenfeld Pearlstein, LLC

(57) ABSTRACT

An improved grinder/polisher includes a base having a bowl, a rotating drive plate and a drive plate drive that is adapted to support a platen. The grinder/polisher includes a head configured to support a specimen holder. The head has a first drive for rotational drive of the specimen holder and a second drive for moving the specimen holder toward and away from the drive plate. The head includes a load cell operably connected to the first drive and a counter operably connected to the second drive. The counter is configured to determine movement and the extent of movement of the head toward and away from the drive plate. The grinder/polisher includes a control panel mounted within a housing and including a microprocessor controlled control system having a touch panel or screen.

8 Claims, 13 Drawing Sheets

GRINDER/POLISHER

CROSS-REFERENCE TO RELATED APPLICATION DATA

This application claims the benefit of priority of provisional U.S. Patent application Ser. No. 61/074,455, filed Jun. 20, 2008.

BACKGROUND OF THE INVENTION

The present invention relates to a grinder/polisher. More particularly, the present invention relates to an improved grinder/polisher for preparing samples for examination.

Grinder/polishers are in use in many industries. They are often used to prepare samples of metals, polymers, ceramics or the like for further examination, such as by microscopic examination.

Known grinder/polishers include a sample or specimen holder that is configured to rotate relative to a platen that is also configured to rotate. In this manner, there are two rotating motions occurring simultaneously. A slurry, generally abrasive, is injected onto the platen to provide an abrasive medium for grinding and polishing the specimen.

The specimen holder is supported for rotation in a chuck. The holder is a flat plate with multiple openings in which the specimens reside. In one mode, the specimens are locked into the holder and a downward force by the holder applies a pressure on the platen. As the holder and platen rotate, the pressure applied by the holder (and specimen), along with the abrasive action of the slurry, results in a grinding and polishing action on the specimen.

In another mode, the specimen floats within the holder and a plunger is moved into contact with the specimen to apply pressure to the specimen. Again, as the holder and platen rotate, the pressure applied by the plunger, along with the abrasive action of the slum- results in a grinding and polishing action on the specimen.

Movement of the holder toward and away from the platen is controlled by a drive located in the grinder/polisher head. The drive motor is used to position the holder and thus the specimen relative to the platen. One drawback to known grinder/polishers is that there is no positive positioning control or mechanism to precisely control the position of the holder relative to the platen.

The platen is supported within a bowl. The bowl serves as a repository for debris that is generated during the grinding/polishing operation. Water or another fluid is used to rinse with bowl to clear the debris. It has been found that even with known rinsing systems, debris can collect in the bowl and cause unsightly and inconvenient accumulation in the bowl. It has also been found that if a grind is particularly aggressive, the platen can heat up which, it is believed, can adversely effect specimen preparation.

Accordingly, there is a need for an improved grinder/polisher. Desirably, such a grinder/polisher includes an improved illumination system to enhance the visibility of the working area. More desirably, such a grinder/polisher has an improved rinsing/bowl clearing system. More desirably still, such a grinder/polisher has an improved system for positioning the head and specimen holder and for holding the specimens in position relative to the rotating platen.

BRIEF SUMMARY OF THE INVENTION

An improved grinder polisher includes a base having a bowl, a rotating drive plate, a drive plate drive and a control system. The drive plate is adapted to support a platen.

The grinder/polisher includes an improved illumination system to enhance the visibility of the working area and has an improved rinsing/bowl clearing system. An improved system is also provided for positioning the head and specimen holder and for holding the specimens in position relative to the rotating platen.

In a present embodiment, the head is configured to support the specimen holder. The grinder polisher includes, housed within the head, a first drive for rotational drive of the specimen holder (a rotational drive) and a second drive for moving the head and the specimen holder vertically, toward and away from the platen (a height drive).

The head includes a load cell operably connected to the first drive and a counter configured to determine movement and the extent of movement of the head toward and away from the plate.

The load cell is adapted to sense contact between the specimen holder and the platen when the second drive is operating in a forward direction (to move the specimen holder into contact with the platen) and to stop movement in the forward direction upon sensing contact between the holder and the platen. In a present system, in one mode of operation, the control system is configured so that following sensing contact between the specimen holder and the platen, the second drive is stopped and reversed to move the specimen holder away from the platen a predetermined distance. In this operating mode, the specimens are then positioned in the holder. The specimens are held in place by fingers during the grinding/polishing operation. The fingers are extendable from and retractable into a portion of the head that is rotatable with the specimen holders. The fingers are configured to contact the specimens and apply a pressure on the specimens to engage the specimens with the platen.

In a present embodiment the fingers are biased to the retracted position and means are present for extending the fingers. The fingers are formed from a base material having a coating thereon. One suitable coating is a ceramic material.

In another mode of operation, the control system is configured so that the load cell senses a load generated by contact between a specimen and the platen and generates a signal to actuate the second drive to operate in a forward direction to move the specimen toward the platen as the load changes. The grinding/polishing operation can be carried out based upon a predetermined period of operating time or distance moved (e.g., grinding that has occurred).

The grinder/polisher includes a main drive shaft operably connected to the specimen holder and operably connected to the load cell, wherein a force exerted on the main drive shaft provides the sensing of the load generated by contact between the specimen and the platen.

The height drive includes a lead screw for moving the specimen holder toward and away from the platen. The lead screw is operably connected to the counter. A carriage and rails are provided for guiding the head and the specimen holder toward and away from the platen.

The control system is housed, at least in part, in a housing and includes a microprocessor controlled control system. The control system includes a touch panel or screen.

The improved grinder polisher can also include a replaceable bowl liner for fitting into the bowl. In a present grinder polisher the bowl and bowl liner have a general D-shape to define spaces between the periphery of the platen and the bowl liner for hand access to the platen. The bowl liner can be transparent and formed from plastic.

The grinder polisher can also include lighting disposed in the head directed toward the platen and bowl. The lighting is preferably provided by LEDs.

These and other features and advantages of the present invention will be readily apparent from the following detailed description, in conjunction with the claims

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying and drawings, wherein.

DETAILED DESCRIPTION OF THE INVENTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Referring now to the figures and in particular, to FIGS. 1-4, there is shown an improved grinder/polisher 10. The grinder/polisher 10 includes, generally, a base 12, a head 14 and a control panel 16. Unlike known grinder/polishers, the casing 18 of the present device 10 is fabricated from a cast material. A present material is a cast aluminum. Known grinder/polishers are fabricated from sheet material (sheet metal) or a plastic over a supporting frame. As such, known grinder/polishers can be subjected to vibration, damage due to use and the like. The present cast body (head 14, base 12 and control panel housing 20) provide a stable support structure for the grinder/polisher 10, even under aggressive grinding conditions.

The base 12 houses the platen 22, the platen drive 24, and the fluid supply and rinse components 26. The base 12 also houses a collection bowl or basin 28 in which the fluid is collected, as well as debris that is generated during grinding/polishing.

As will be appreciated, there can be a considerable amount of debris that is generated during operation, and as such, debris build-up on the bowl 28 can be problematic. In many cases, the debris hardens and is difficult and time consuming to remove. It has been observed that in some instances, when the debris has been allowed to accumulate too much and has hardened, it can be almost impossible to remove. At times, the amount of force required to break away the debris is so great, that it has resulted in damage to these known grinder/polisher bowls.

Figure 28:
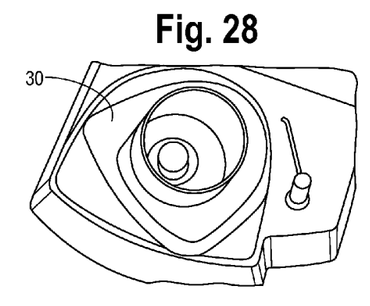
FIG. 28 illustrates a clear liner for placement in the bowl.
Figure 29:
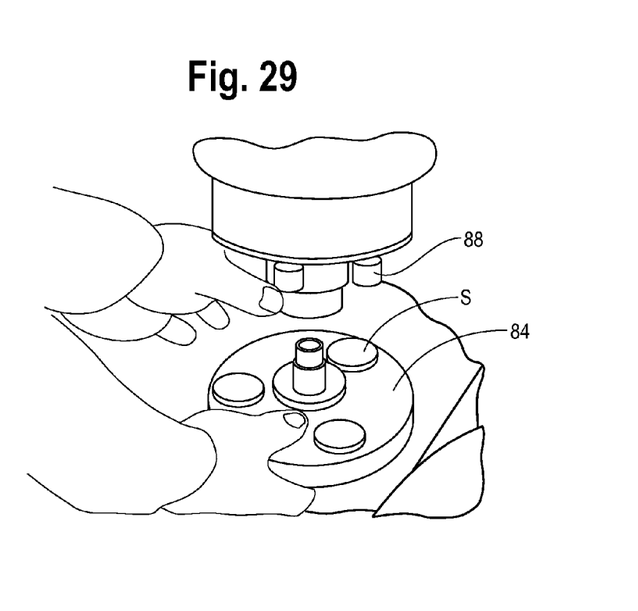
FIG. 29 shows the ready installation of the specimen holder.
Figure 30:
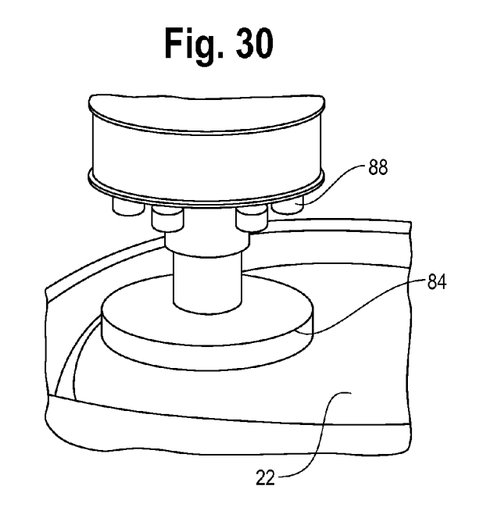
FIGS. 30 and 31 illustrate one of the fingers retracted and extended for grinding/polishing.
Figure 31:
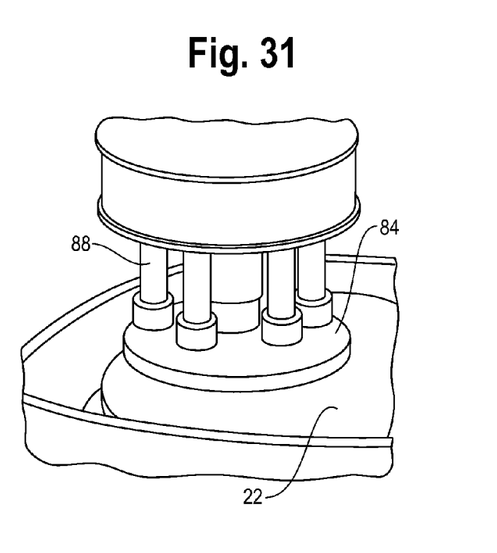

To alleviate this condition, the present grinder/polisher 10 includes a removable/replaceable/disposable bowl liner 30 (see FIG. 28). This, of course, resolves the unsightly or even non-functional condition due to over-accumulation by employing a bowl liner 30 that can be removed or replaced to facilitate cleaning, and that is intended to be disposed of, if necessary, so that a new functional bowl liner is readily installed on the grinder/polisher 10. A present bowl liner 30 is preferably formed from a plastic material and more preferably a transparent plastic material to permit viewing the bowl as needed.

The fluid supply and rinse 26 includes a hose/dispenser assembly 32 mounted to the base 12 (see FIGS. 1-4 and 25). The assembly 32 is used to dispense or spray water into the bowl 28 to provide a water supply to help maintain the bowl 28 clear of debris. In a present grinder/polisher 10, the hose 34 is a flexible rubber material stored in the base 12. The hose 34 can be stored in a system (not shown) that permits extending and retracting the hose 34 from the 12 for use. The hose 34 has a woven metal sheathing (not shown) to protect the hose 34 and to permit manipulating and positioning the hose 34 as desired.

Figure 5:
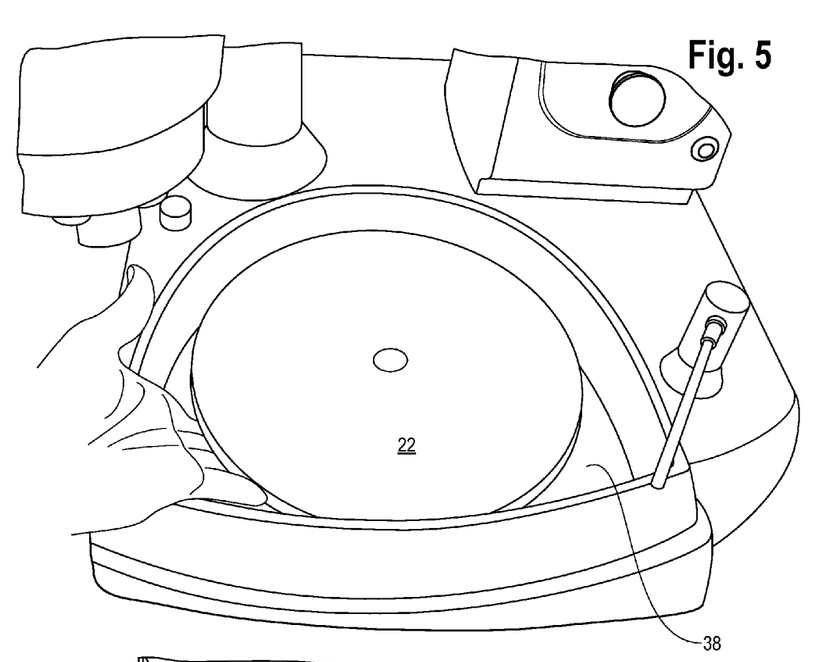
FIG. 5 is a close-up view of the platen shown with a user's hand to illustrate access to the platen.

A splash guard 36 is integral with the base 12 and extends up from the base 12, surrounding the bowl 28. The splash guard 36 and the base 12 at the splash guard 36 integration have a D-shape (as indicated at 37) which provides open corner areas 38 that define hand-holds (see FIG. 5), so that an operator can access the area inside of the bowl 28, within the area bounded by the splash guard 36.

The platen 22 is removable and is mounted to a drive plate 40 that is driven, by a belt 42, from a platen drive motor 43 and form part of the platen drive 46 (see FIGS. 9, 18 and 21-23). The drive plate 40 and platen 22 are configured to rotate clockwise or counterclockwise, typically from about 10 rpm to about 500 rpm. A high torque motor 43 is used to assure constant platen 22 speed and torque, regardless of the applied load.

The drive plate 40 includes openings 44 in the bottom thereof so that water can enter up through the drive plate 40 onto the underside of the platen 22. One preferred platen 22 has fins or spokes (not shown) on the underside that direct water outwardly. This facilitates cooling the platen 22 from underneath. It has been observed that when a grind is particularly aggressive, the platen 22 may tend to heat, which, in turn may have an adverse effect on the specimen being prepared. Accordingly, platen 22 cooling helps to maintains the platen 22 at a more optimal operating temperature The head 14 supports and rotates the specimens S. The head 14 is mounted to the base 12 by a telescoping support 48. The head 14 contains two drive systems 50, 52—one drive system 50 for rotation of the specimen holder 84 via the chuck 54, and a height drive system 52 for up and down movement of the head 14 to move the specimen holder 84 and the specimens S toward and away from the platen 22. The movements, rotational and height, are provided by the separate drive systems 50, 52.

The rotational drive 50 (see FIGS. 14-17) is configured to rotate the specimen holder 84 in either a clockwise or counter clockwise direction. In a present grinder/polisher 10, the drive system 50 is a gear 51 drive, driven by a motor 53, however, a direct drive, belt drive or the like can also be used. It will be understood that the head 14 is stationary as the specimen holder 84 rotational drive 50 is operating. The drive system 50 includes a can-like housing 57 that has a gear 55 that engages the motor gear 51 to rotate the can-like housing 57.

The height drive 52 (see FIGS. 12-13 and 15) is a precision drive to precisely position the specimen holder 84 and the specimens S relative to the platen 22. The height drive 52 is fixedly mounted in the head 14. The present grinder/polisher 10 uses a servomotor 54 that is operably connected, by a timing belt 56 to a pulley 58 (driven by the belt 56). A lead screw 60 is mounted to the pulley 58 for rotation with the pulley 58. The lead screw 60 is mounted to a fixed (relative to the base 12 and the support 48) threaded receiving element 62 so that rotation of the lead screw 60 moves the head 14 up and down to move the specimen holder 84 toward and away from the platen 22.

The height drive system or assembly 52 includes rails 64 and rollers/bearings 66 to provide an underlying support structure and to facilitate smooth and guided movement of the head 14 as it moves in the up and down motion (by action of the lead screw 60).

Figure 13:
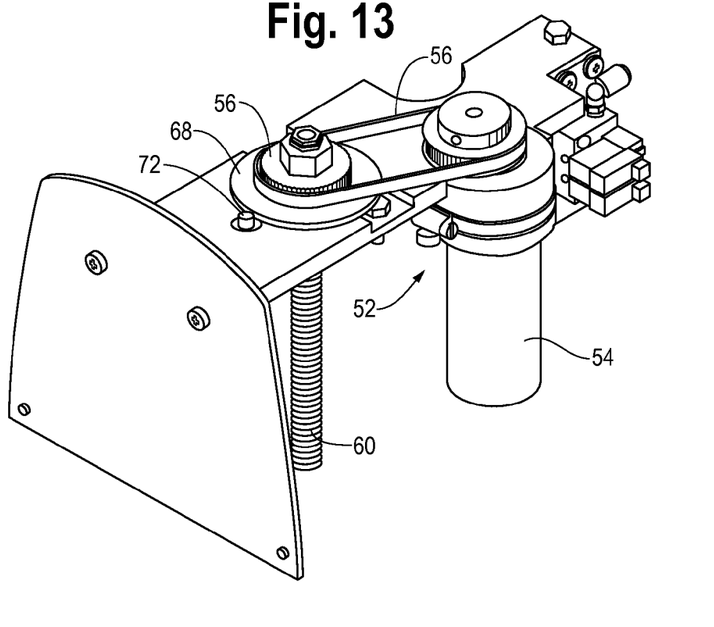
FIG. 13 is a partial view of the height drive assembly
Figure 15A:
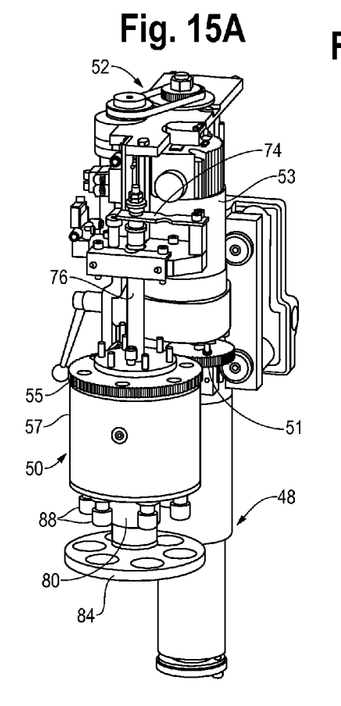
FIGS. 15A-C are perspective and elevational views of portions of the specimen (rotational) drive and chuck, shown with a specimen holder therein and the specimen drive assembly shaft and chuck and the specimen holding fingers.
Figure 15B:
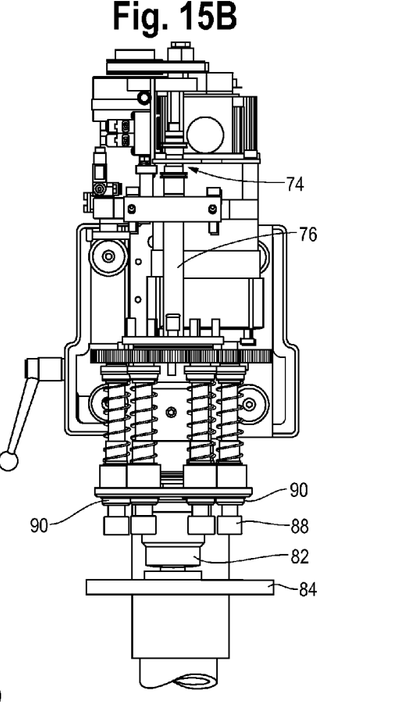
Figure 15C:
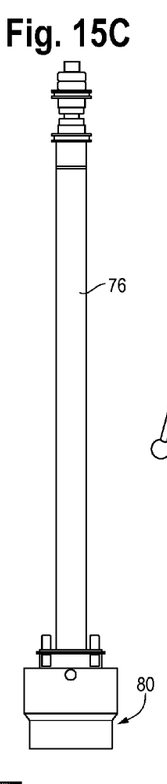

In order to precisely locate the head 14 height relative to the platen 22 (and the base 12), the height drive 52 includes a lead screw gear 68 and counter 70, to count the relative rotation of the lead screw 60 (see FIGS. 13 and 15). The lead screw gear 68 sits below and is fixedly mounted to the pulley 58 and the lead screw 60. The counter 70 is driven by a pinion gear 72 that is meshed with the lead screw gear 68. In this manner, the number of rotations of the lead screw gear 68, which is equal to the number of rotations of the lead screw 60, is counted by the rotations of the pinion gear 72, which correlates to the height travel of the lead screw 60. As such, from a baseline position, the height of the head 14 (and thus the height or distance of the specimens S from the platen 22) can be readily determined. It will be appreciated from the figures that the lead screw gear 68 is quite large relative to the pinion gear 72 (and thus the counter 70), and as such there is the ability to monitor and control, to a very precise degree, the rotation of the lead screw 60. This in turn provides the ability to precisely control the travel of the head 14 relative to the platen 22.

Although a lead screw 60 and counter 70 arrangement is shown, those skilled in the art will recognize other ways in which precise control of the specimen S height, relative to the platen 22, can be determined and controlled.

Figure 14:
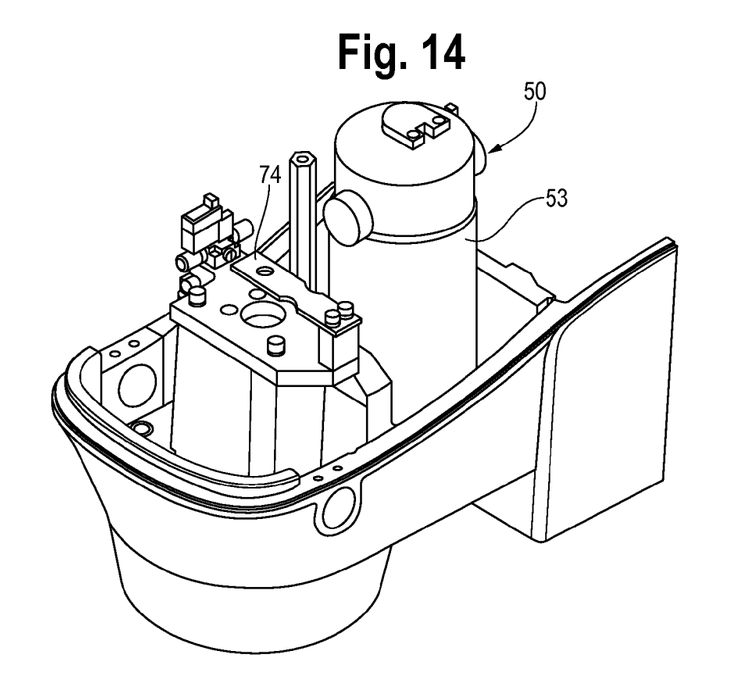
FIG. 14 is a perspective view of a portion of the rotational drive assembly.

The head 14 also includes a load cell 74 (see FIGS. 14-15B). The load cell 74 is configured to sense the weight load that is placed on the rotational drive motor 53 and drive assembly 50 by the specimens S and holder 84 when they are mounted to the drive 50 (at the chuck 80). The load cell 74 is also configured to determine when the specimen holder 84, "hanging" from the motor 53, comes into contact with the platen 22 (by sensing an upward force or load differential at the load cell 74). The load cell 74 is disposed above the main drive shaft 76.

Figure 6:
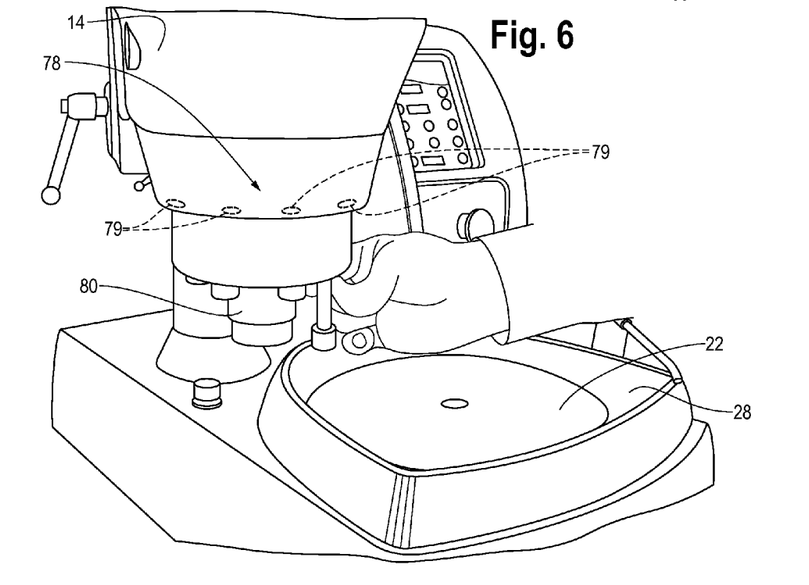
FIG. 6 illustrates one of the fingers extended (by a user's hand) for ease of illustration, also noted are the LEDs for work area illumination.
Figure 7:
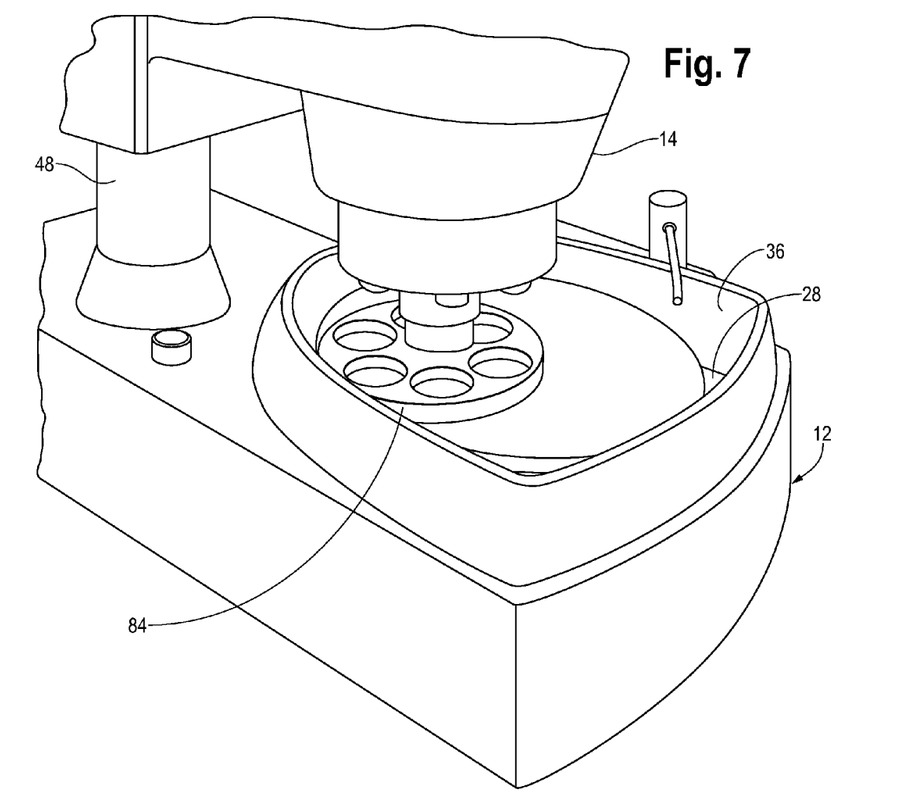
FIG. 7 is a perspective view showing the platen and a central mode specimen holder in position for operation, also noted is the dispenser portion of the hose (the hose not shown) positioned over the bowl.

Unlike known grinder/polishers, the present grinder/polisher head 14 includes integrated lighting 78 (see FIG. 6). In a present grinder/polisher 10, light emitting diodes (LEDs) 79 are mounted to the head 14, to illuminate the holder 84 and specimens S and the platen 22 (the work area generally), including the bowl 28. Compact, built-in illumination provides for better viewing of and thus control over the grinding/polishing process. A present grinder/polisher 10 includes nine LEDs spaced around the periphery of the head 14 for work area/specimen S illumination. It will be appreciated that the LEDs 79 do not rotate with the chuck 80 but are stationary as mounted within the head 14.

Figure 8:
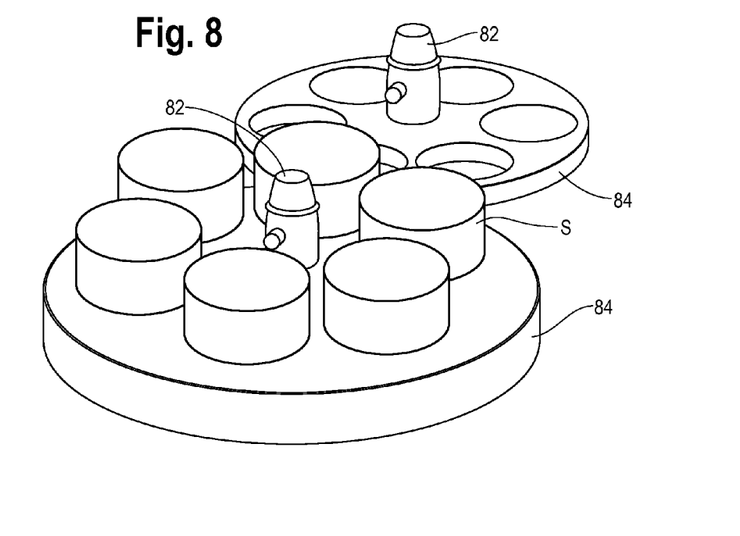
FIG. 8 is an illustration of a central mode specimen holder with specimens mounted therein in the foreground and a single mode specimen holder in the background.
Figure 9:
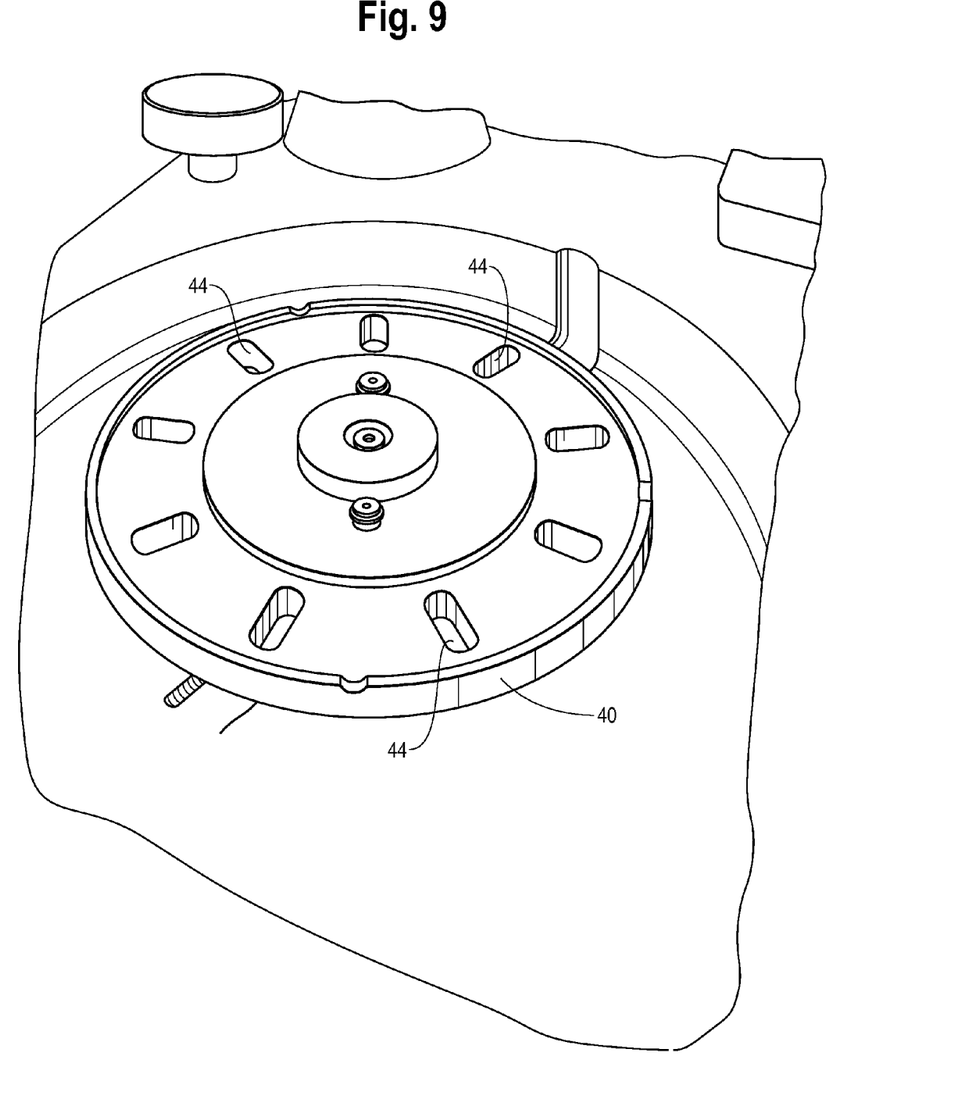
FIG. 9 illustrates the drive plate, showing the openings in the drive plate and also showing, in part, the bowl drain.
Figure 10A:
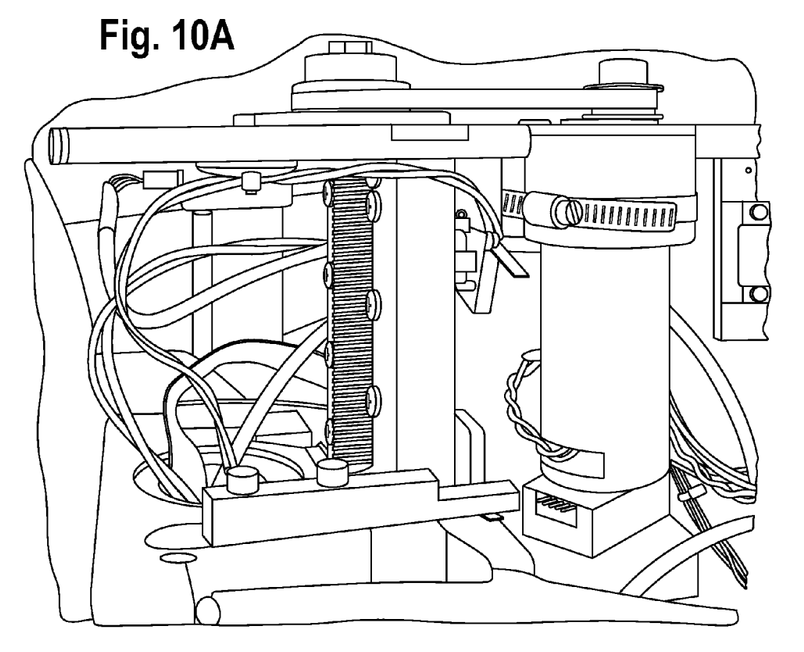
FIGS. 10A and 10B are elevational and perspective views of the head (height) drive assembly showing the main shaft and load cell.
Figure 10B:
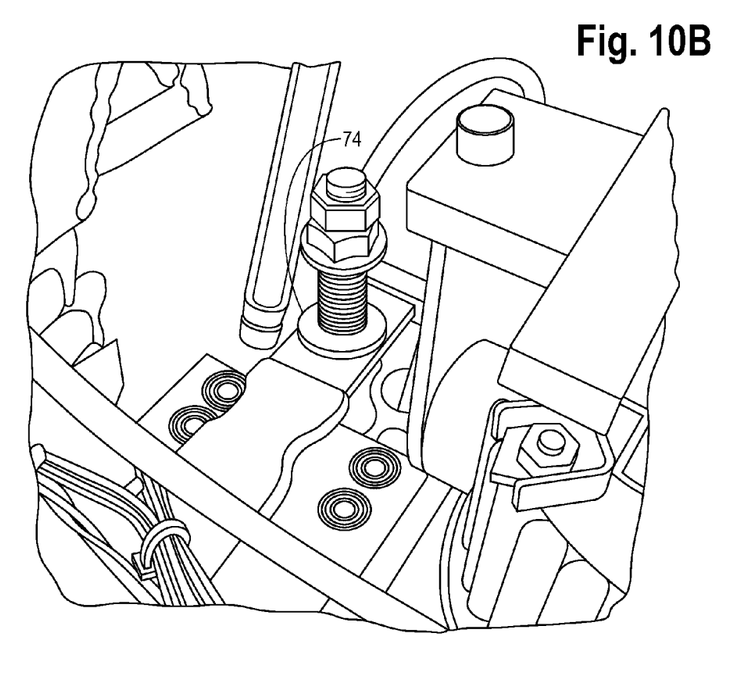
Figures 11, 12A, 12B:
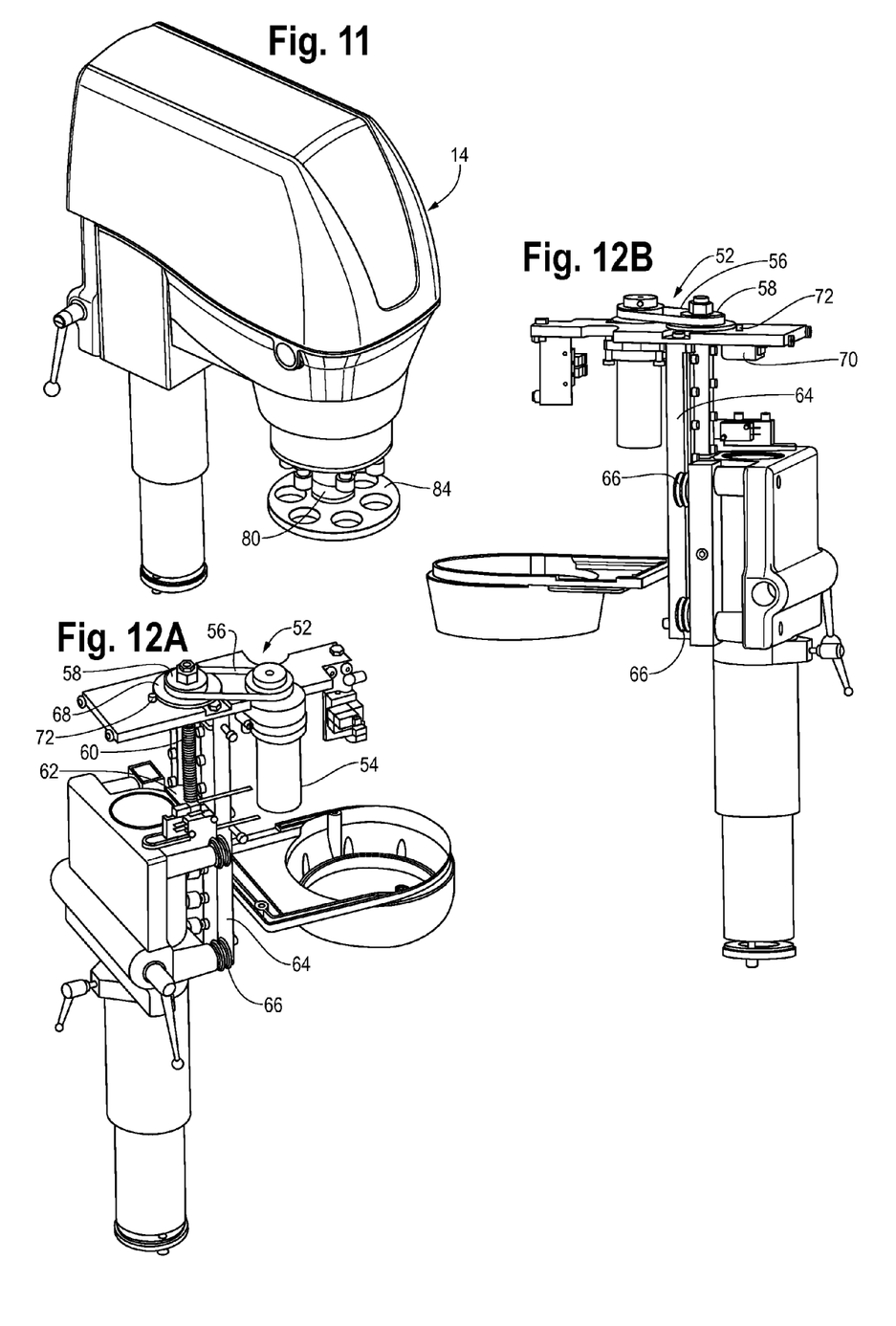
FIG. 11 is a perspective illustration of the head with a specimen holder mounted thereto.
FIGS. 12A-B are illustrations of the head showing the height drive assembly and having portions of the head removed for clarity of illustration.
Figure 16:
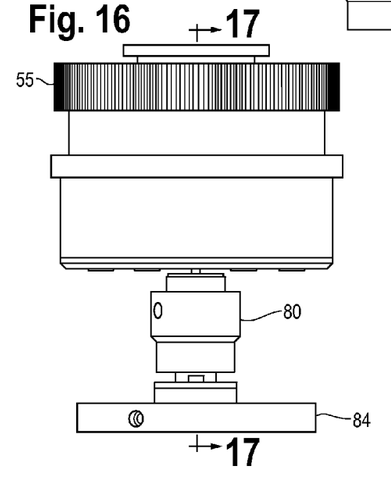
FIGS. 16-17 are elevation and sectional views of the specimen (rotational) drive and chuck.
Figure 17:
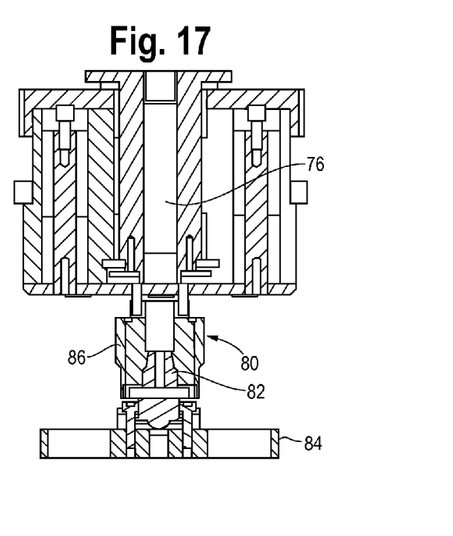
Figure 18:
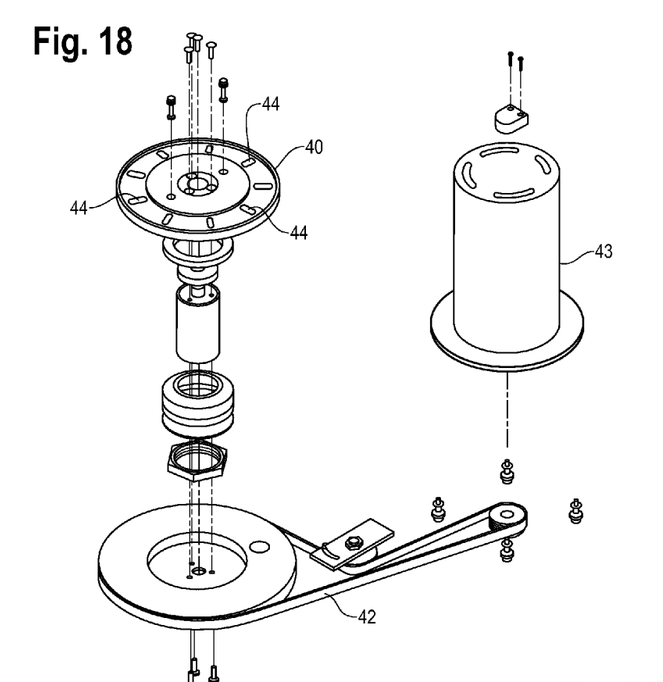
FIG. 18 is an exploded view of the platen drive and drive assembly.

The chuck 80 is operably mounted to the main drive shaft 76 (see FIGS. 15C, 16-17). The chuck 80 is configured for securing the specimen holder 84 thereto. The chuck 80 is adapted to receive a drive adapter 82 that is mounted to the specimen holder 84. One preferred adapter 82 is a tapered adapter (see FIGS. 8 and 17) which permits controlling the force to the bottom of the sample holder 84 to lower the center of gravity. It also permits readily changing the specimen holder 84 with a single pull of the clamping ring 86.

For the single mode of operation, the grinder/polisher 10 includes pneumatically actuated fingers 88 that extend from and retract into the head 14 to contact the specimens S. In this mode of operation, the specimens S "float" in the specimen holder 84 (the specimens S are not fixed within the holder 84), and the pneumatically actuated fingers 88 hold down the specimen S within the confines of the holder 84, against the platen 22.

The fingers 88 are actuated by a pneumatic system (not shown) within the housing 14. The fingers 88, of course, rotate with the chuck 80 and the specimen holder 84 to apply a force on the specimens S during operation. The fingers 88 are formed from a metal core, such as aluminum, and can be ceramic coated (for example, a baked on ceramic) to reduce friction in the bushing 90 at the head 14 (see FIG. 15B). The core or base material of the fingers 88 is selected to provide increased rigidity and stability of the fingers 88.

In the central mode of operation, the specimens S are secured in the holder 84 and the holder 84 is secured in the chuck 80. Because the specimens S are secured in the holder 84, the fingers 88 (to hold down the specimens S) are not required for operation.

Figure 1:
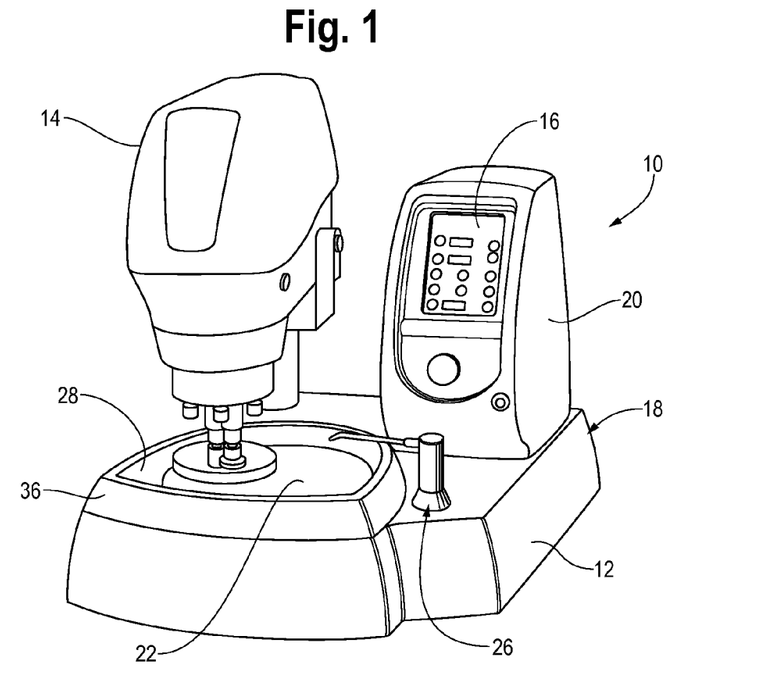
FIG. 1 is a perspective view of the improved grinder/polisher embodying the principles of the present invention.
Figure 2:
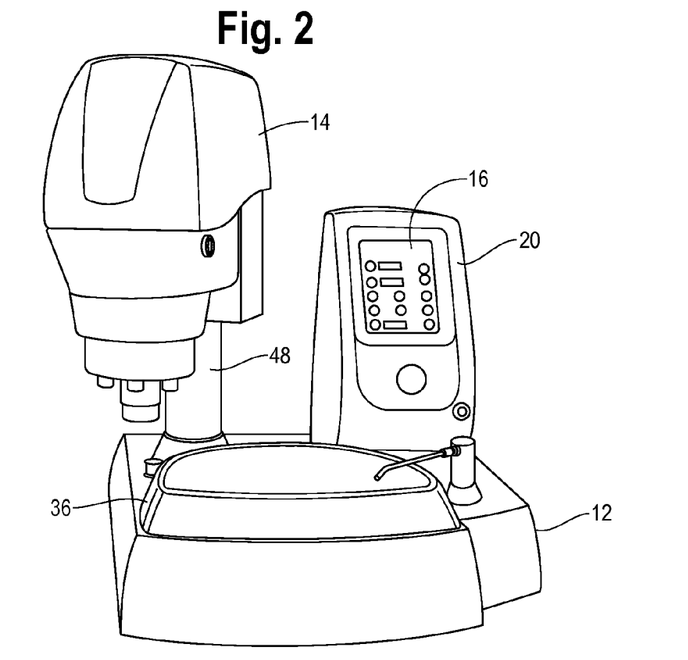
FIG. 2 is a front view of the grinder/polisher shown with the head rotated slightly away from the base.
Figure 3:
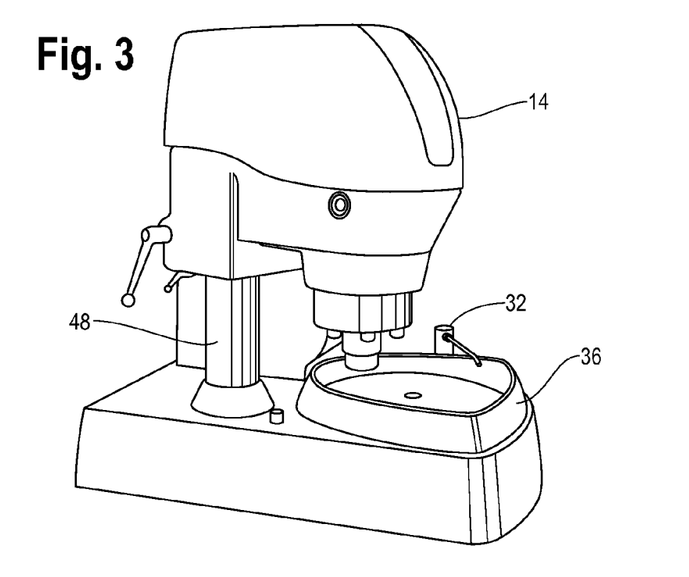
FIG. 3 is a side view of the grinder/polisher.
Figure 4:
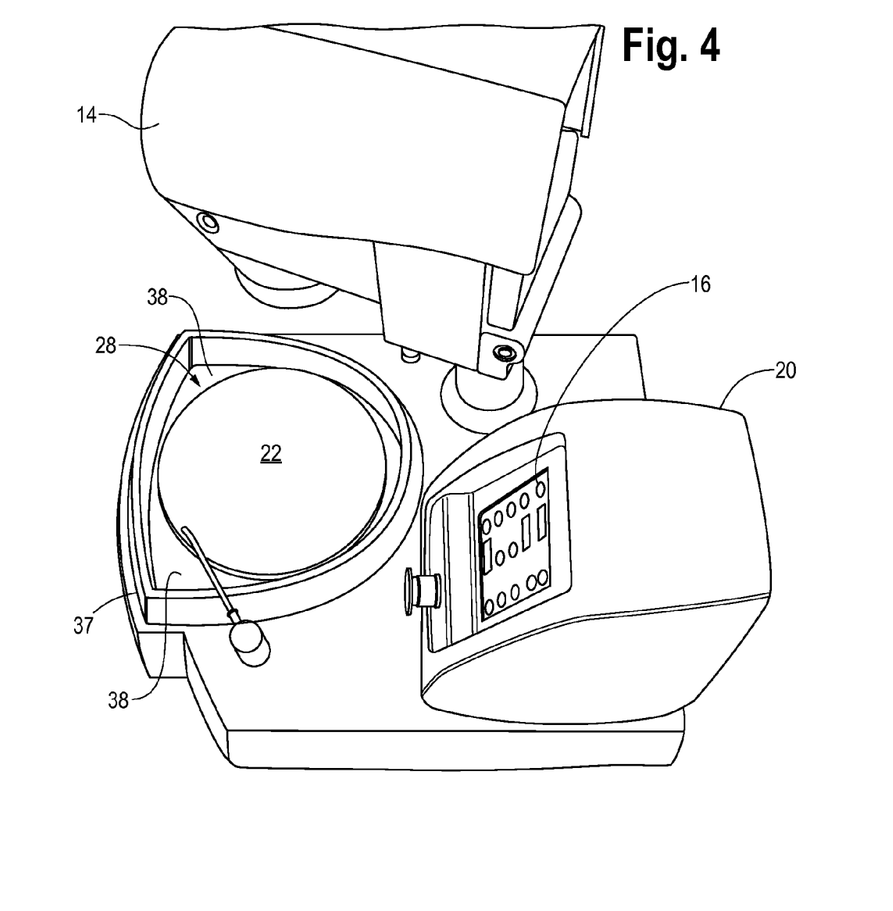
FIG. 4 is a top view showing the platen and the hand-holds provided by the D-shaped base and splash guard, the grinder/polisher also shown with the head rotated slightly away from the base.
Figure 19:
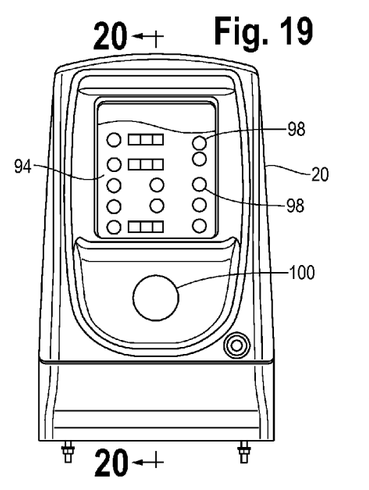
FIGS. 19-20 are front and sectional views of the control system and housing, FIG. 20 being taken along the line 20-20 in FIG. 19.
Figure 20:
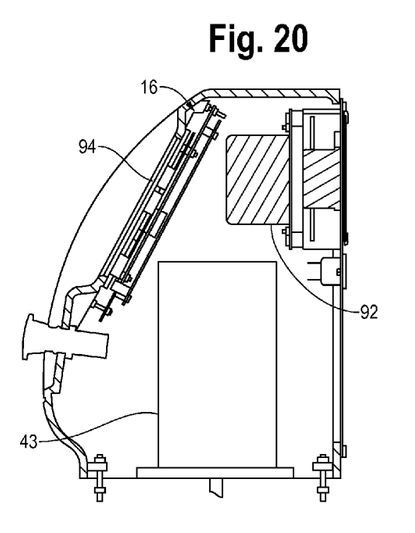
Figure 21:
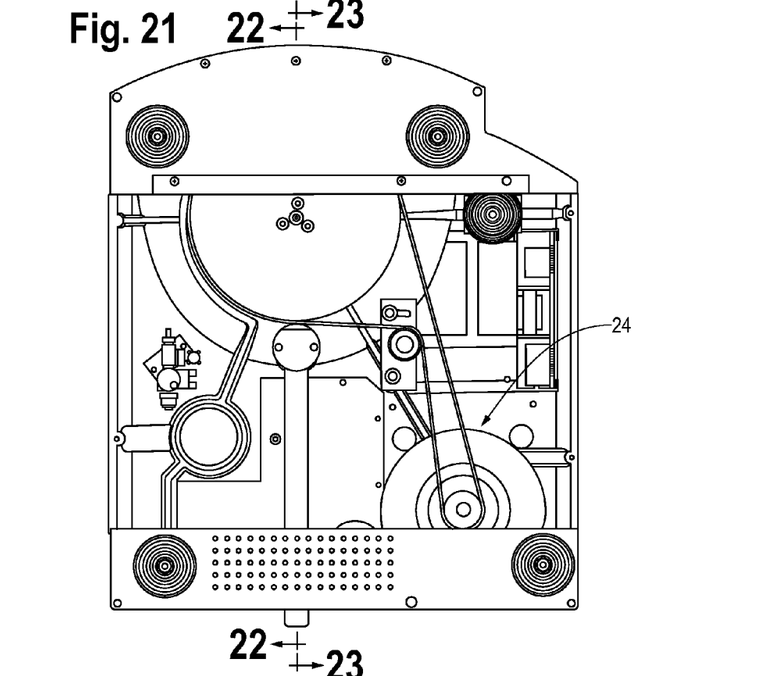
FIGS. 21-23 are bottom and sectional views of the base, FIGS. 22 and 23 taken along lines 22-22 and 23-23, respectively in FIG. 21.
Figure 22:
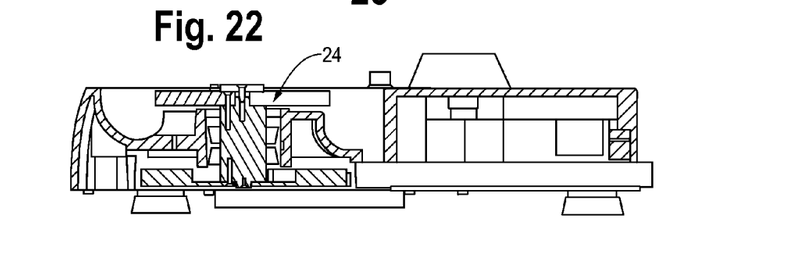
Figure 23:
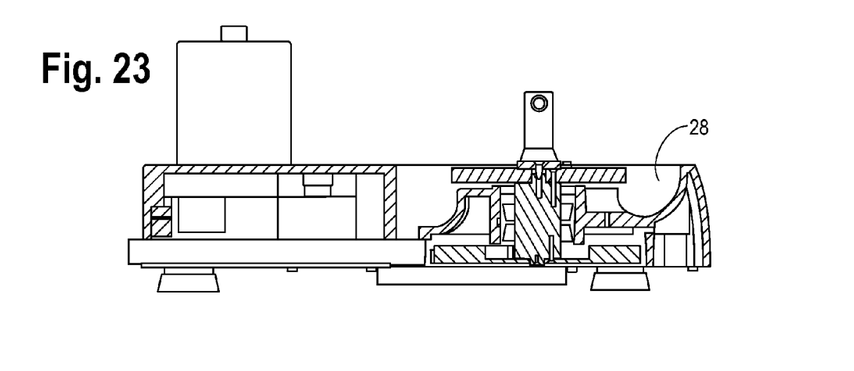
Figure 24:
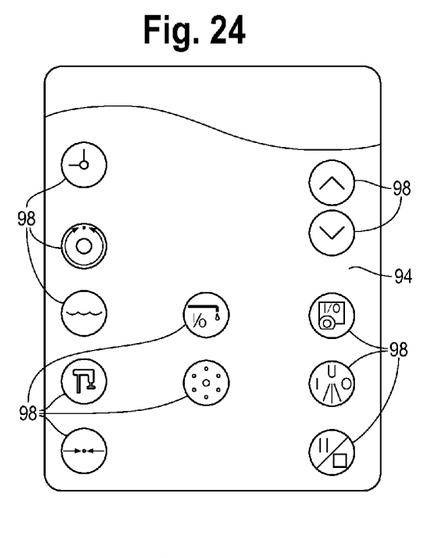
FIG. 24 illustrates some of the icons on the control system screen.
Figure 25:
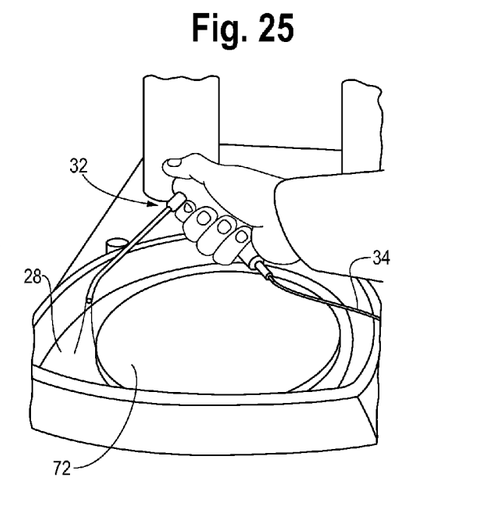
FIG. 25 is a partial perspective illustration of the dispenser with the hose extended for rinsing the platen and bowl.
Figure 26:
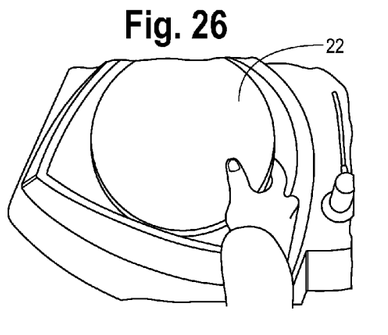
FIG. 26 illustrates removal of the platen.
Figure 27:
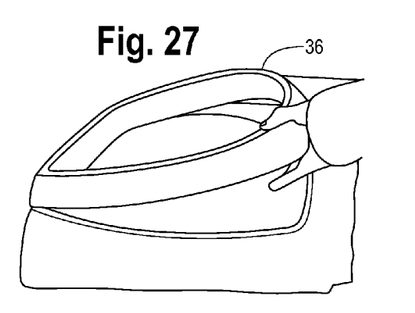
FIG. 27 illustrates removal of the splash guard.

Referring to FIGS. 1 and 19-20, the control panel 16 is mounted to the housing 20 (see FIGS. 1 and 16). In a present grinder/polisher 10, a microprocessor based control system 92 controls the operation of the machine 10. The control panel 16 is a touch screen 94 or plastic/mylar overlay on a contact-type panel 96. This arrangement prevents the ingress of water or other liquids or contaminants into the electrical/electronics area of the control system 16. One additional advantage of the touch screen panel 16 is that icons (see 98 in FIG. 24) can be used or the icons can appear only as applicable to a particular operating mode. For example, if a particular operating step is only applicable to the single mode of operation, and the single mode of operation is entered into system (a single mode button is touched), then only icons that pertain to the single mode of operation can appear on the screen. A stop switch 100 is located on the control panel housing as well.

In the single mode of operation, the head 14 starts from a home position (an up or retracted position), with the holder 84 in the chuck 80. The weight load exerted by the specimen holder 84 is sensed by the load cell 74.

The holder 84 moves down (the height drive 52 actuates), until it contacts the platen 22. Contact is determined by sensing a change in the load on the load cell 74 (to a predetermined differential). Once it is determined that the holder 84 has contacted the platen 22, downward motion is slopped, and the motor 54 reverses to elevate the holder 84 (or back off) from the platen 22 a predetermined distance. In a present grinder/polisher 10 operation, the head 14 backs off about 2 mm after contact. The specimens are then positioned in the holder 84, and the fingers 88 drop down to contact the specimens S to hold the specimens S in place. The head rotational drive system 50 is actuated and the platen 22 commences rotation to grind/polish the specimens S.

In the central mode of operation, the specimens S are fixed in the holder 84. The holder 84 moves down (the height drive 52 is actuated), until a desired force is sensed, and the platen 22 and head rotational 50 drives 24, 53 are actuated to rotate the platen 22 and head (to rotate the chuck 80 and specimens S). Typically, the drive 50 is actuated for a predetermined period of time to grind/polish the specimen. The height drive 52 can be actuated (based upon the load sensed by the load cell 74, and a preset desired load), to move the holder 84 and specimens downward toward the platen 22 as polishing/grinding progresses and material is removed from the specimen.

It will be appreciated that the microprocessor-based control system 16 provides extreme flexibility in operating the grinder/polisher 10. And, in conjunction with the load cell 74 and the lead screw 60/counter 70 drive system, the microprocessor-based control system 16 provides a wide array of controls not known in prior grinder/polisher systems.

It will be understood that the grinding/polishing operation (referred to as preparation) can be based upon a desired time of preparation at a desired force. It can also be based upon a desired amount of material to be removed from the specimen S. For example, the control system 16 can be set to apply a desired force on the specimen S. As specimen preparation is carried out, the load on the load cell 74 is sensed, and the height system 52 motor is actuated to maintain the load within a certain range. The counter 70 is used, to determine the amount of specimen S that has been removed, by sensing (counting) the number of rotations of the lead screw 60 and determining a distance traveled by the head 14, which corresponds to the amount of material removed from the specimen S. Other modes of operation and control will be appreciated by those skilled in the art.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the invention.

What is claimed is:

1. An improved grinder polisher, comprising:
a base having a bowl, a rotating drive plate and a drive plate drive, the drive plate adapted to support a platen;
a head configured to support a specimen holder and having a first drive for rotational drive of the specimen holder, the head having a second drive for moving the head and the specimen holder toward and away from the platen, the head including a load cell operably connected to the first drive and a counter configured to determine movement and the extent of movement of the head toward and away from the platen;
a lead screw for moving the specimen holder toward and away from the platen, the lead screw being connected to the counter, wherein a lead screw gear is mounted to the lead screw, and the counter is driven by a pinion gear that is meshed with the lead screw gear, wherein the lead screw gear is larger than the pinion gear; and
a control system.

2. The grinder/polisher in accordance with claim 1 wherein the load cell is adapted to sense contact between the specimen holder and the platen when the second drive is operating in a forward direction to move the specimen holder into contact with the platen and to stop movement in the forward direction upon sensing contact.

3. The grinder/polisher in accordance with claim 2 wherein following sensing contact between the specimen holder and the platen, the second drive is stopped and reversed to move the specimen holder away from the platen a predetermined distance.

4. The grinder/polisher in accordance with claim 2 including a main drive shaft operably connected to the specimen holder and operably connected to the load cell, wherein a force exerted on the main drive shaft provides sensing of a load generated by contact between the specimen holder and the platen.

5. The grinder/polisher in accordance with claim 1 wherein the load cell is configured to sense a load generated by contact between a specimen and the platen and, when the grinder/polisher is operating, generate a signal to actuate the second drive to operate in a forward direction to move the specimen toward the platen as the load changes.

6. The grinder/polisher in accordance with claim 1 including a carriage and rails for moving the head and the specimen holder toward and away from the platen.

7. The grinder/polisher in accordance with claim 1 wherein the control system is housed, at least in part in a housing and including a microprocessor controlled control system.

8. The grinder/polisher in accordance with claim 7 wherein the control system includes a touch panel or screen.

\* \* \* \* \*

UNITED STATES PATENT AND TRADEMARK OFFICE
CERTIFICATE OF CORRECTION

| | | |
|---|---|---|
| PATENT NO. | : 8,574,028 B2 | Page 1 of 1 |
| APPLICATION NO. | : 12/470757 | |
| DATED | : November 5, 2013 | |
| INVENTOR(S) | : Shewey et al. | |

It is certified that error appears in the above-identified patent and that said Letters Patent is hereby corrected as shown below:

In the Specification

On column 1, line 36, "slum-" to read as --slurry--.

On column 2, line 16, "plate." to read as --platen.--.

On column 3, line 3, "claims" to read as --claims.--.

On column 3, line 44, "assembly" to read as --assembly;--.

On column 4, line 55, "new" to read as --new,--.

On column 5, line 28, "temperature" to read as --temperature.--.

On column 7, line 32, "slopped," to read as --stopped,--.

Signed and Sealed this
Thirteenth Day of January, 2015

Michelle K. Lee
*Deputy Director of the United States Patent and Trademark Office*